United States Patent [19]

Lengnick

[11] 4,033,902

[45] July 5, 1977

[54] COBALT-PLATINUM CATALYST

[75] Inventor: Guenther Fritz Lengnick, Adrian, Mich.

[73] Assignee: SWS Silicones Corporation, Adrian, Mich.

[22] Filed: July 21, 1975

[21] Appl. No.: 597,940

Related U.S. Application Data

[60] Continuation-in-part of Ser. No. 471,750, April 20, 1974, abandoned, which is a continuation of Ser. No. 273,676, July 20, 1972, abandoned, which is a division of Ser. No. 214,445, Dec. 30, 1971, Pat. No. 3,714,212.

[52] U.S. Cl. .............. 252/441; 252/443; 423/416; 423/417; 423/462; 423/463
[51] Int. Cl.$^2$ .......... B01J 27/06; B01J 27/20; C01G 1/04; C01B 9/00
[58] Field of Search .......... 423/463, 462, 416, 417, 423/438, 72, 138; 252/441, 443

[56] References Cited

UNITED STATES PATENTS

| | | | |
|---|---|---|---|
| 2,691,046 | 10/1954 | Hasek | 252/443 X |
| 3,097,237 | 7/1963 | Sauer | 252/441 X |
| 3,168,553 | 2/1965 | Slaugh | 252/441 X |
| 3,865,858 | 2/1975 | Ossko et al. | 252/441 X |

OTHER PUBLICATIONS

Hand Book of Chemistry and Physics 42nd Edition, 1961, The Chemical Rubber Publishing Co., Ohio, pp. 564–565.

*Primary Examiner*—Winston A. Douglas
*Assistant Examiner*—William G. Wright

[57] ABSTRACT

The invention relates to a cobalt-platinum catalyst for promoting the addition of ≡ Si-H compounds to unsaturated organic compounds which comprises reacting platinum dichloride with dicobalt octacarbonyl in the presence of an inert solvent at a temperature up to about 52° C.

4 Claims, No Drawings

COBALT-PLATINUM CATALYST

This application is a continuation-in-part of continuation application Ser. No. 471,750 filed on Apr. 20, 1974, now abandoned, which was a continuation of application Ser. No. 273,676, filed on July 20, 1972, now abandoned, which was a division of application Ser. No. 214,445, filed on Dec. 30, 1971, and issued as U.S. Pat. No. 3,714,212 on Jan. 30, 1973.

The present invention relates to a novel catalyst and particularly to a novel catalyst for effecting the addition of organosilicon compounds to unsaturated organic compounds, and esterification of the organosilicon compounds with compounds having an active hydrogen. More particularly the invention relates to a cobalt catalyst for effecting the addition of silicon bonded hydrogen compounds for effecting the addition of silicon bonded hydrogen compounds to aliphatic unsaturated organic compounds and esterification of silicon bonded hydrogen compounds with organic compounds having an active hydrogen.

Heretofore, various platinum catalysts and complexes thereof have been used in the preparation of various organosilicon compounds. These platinum catalysts included compounds such as chloroplatinic acid, various platinum chloride-ethylene complexes, platinum chloride-cyclopropane catlysts and various complexes derived by reacting alcohols, ethers and aldehydes with chloroplatinic acid.

It is therefore an object of this invention to provide a novel catalyst. Another object of this invention is to provide a novel cobalt-platinum catalyst. Another object of this invention is to catalyze the addition of ≡Si—H containing compounds to unsaturated organic compounds in the presence of a cobalt-platinum catalyst at low temperatures. A further object of this invention is to catalyze the esterification of ≡Si—H containing compounds to organic compounds having an active hydrogen.

The foregoing objects and others which will become apparent from the following description are accomplished in accordance with this invention, generally speaking, by reacting in the presence of a catalyst having the empirical formula $(CO)_8(CO)_2Pt(Cl)_2$, a compound containing a silicon bonded hydrogen group (≡Si—H) and a compound having carbon-to-carbon unsaturation, (C=C) or a compound having an active hydrogen.

Various methods may be used to prepare the platinum catalyst of this invention. For example, platinum dichloride may be reacted with dicobalt octacarbonyl in the presence of an inert solvent at a temperature up to about 52° C. and more preferably at temperatures of from about 30° to 52° C. and thereafter washed with an inert nonsolvent such as ligroin to provide a compound having the empirical formula $(CO)_8(CO)_2Pt(Cl)_2$.

Suitable inert solvents which may be employed are ethers having boiling points up to about 120° C., preferably ethers having boiling points below about 80° C. Examples of suitable ethers are alkyl ethers such as dimethylether, diethylether, methyl ethyl ether, n-propyl ether, isopropyl ether, methyl-n-propyl ether, methyl isopropyl ether, methyl n-butyl ether, ethyl n-propyl ether, ethyl isopropyl ether; cyclic ethers such as tetrahydrofuran, dimethyl furan, 1,4 dioxane and the like.

The reaction may be conducted at atmospheric, superatmospheric or subatmospheric pressures.

The mol ratio of platinum dichloride to dicobalt octacarbonyl should be about 1:1 in order to prepare the desired cobalt-platinum catalyst.

The cobalt-platinum catalyst of this invention is effective for the addition of an unlimited class of organosilicon compounds having carbon-carbon unsaturation or compounds having an active hydrogen group. Also, this catalyst is effective for the esterification of ≡Si—H compounds having an active hydrogen.

The organosilicon compounds which contain a silicon-hydrogen bond may be monomeric or polymeric. However, the silicon-hydrogen containing reactant must contain at least one silicon bonded hydrogen atom per molecule and preferably no more than about two hydrogen atoms to any one silicon atom.

Suitable monomeric silicon compounds and organosilicon compounds containing silicon-hydrogen bonds which may be used in the practice of the present invention are those represented by the formula

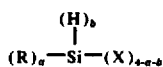

wherein R represents an organic radical, preferably a member selected from the class consisting of monovalent hydrocarbon radicals, halogenated hydrocarbon radicals and cyanoalkyl radicals; X is a member selected from the class consisting of hydrogen, OR radicals and OOCR radicals; $a$ is a number of from 0 to 3; $b$ is a number of from 1 to 2 and the sum of $a$ and $b$ is from 1 to 4. Where more than one R radical is present in the compound, the various R radicals may be the same or different.

Among the radicals represented by R are alkyl radicals, e.g., methyl, ethyl, propyl, octyl, octadecyl and the like; cycloalkyl radicals such as cyclohexyl, cycloheptyl and the like; aryl radicals such as phenyl, naphthyl, tolyl, xylyl and the like; aralkyl radicals such as benzyl, phenylethyl and the like; haloaryl radicals and haloalkyl radicals such as chlorophenyl, chloromethyl, dibromophenyl and the like. In addition to the radicals mentioned above, R may also be an unsaturated aliphatic radical such as vinyl, allyl, cyclohexenyl and the like. In the preferred embodiment, R is methyl or a mixture of methyl and phenyl radicals.

Examples of suitable silicon compounds represented by the above formula which can be employed in the present invention are methyldichlorosilane, phenyldichlorosilane, diethylchlorosilane, dimethylethoxysilane, diphenylchlorosilane, trimethoxysilane, triacetoxysilane, diacetoxyphenylsilane, dichlorosilane, dibromosilane, pentachlorodisiloxane and the like.

Suitable silicon hydrogen containing compounds useful in the practce of the present invention are those in which each molecule contains at least one silicon-hydrogen bond. Within this category are included organopolysiloxanes and various polysilaalkylene compounds containing, for example, a —Si—R'—Si— grouping in which R' is a divalent hydrocarbon radical having from 1 to 8 carbon atoms or a nitrogen atom such as the organosilazanes which are characterized by an —Si—N—Si— linkage in the polymer.

Suitable examples of organopolysiloxanes are polymers and copolymers containing up to one or more of the units having the formulae

along with at least one unit per molecule having the formulae $RHSiO$, $R_2HSiO_{0.5}$, $HSiO_{1.5}$, $H_2SiO$, or $RH_2SiO_{0.5}$ where R is as previously defined. Any of the silicon hydrogen compounds described above are operative in the practice of the present invention; however, it is preferred that the silicon hyrogen compound be an organopolysiloxane such as an organocyclopolysiloxane:

$(RHSiO)_x$ or an organopolysiloxane polymer or copolymer having the formula $(R)_y Si(H)_z O_{\frac{4-y-z}{2}}$ where R is as previously defined; x is a number of at least 3; y is a number of from 0.5 to 2.49; z is a number of from 0.001 to 1 and the sum of y and z is equal to from 1 to 2.5.

Compounds containing carbon-to-carbon unsaturation particularly unsaturated compounds containing olefinic or acetylenic unsaturation which can react with the compounds described above containing the silicon hydrogen linkage includes substantially all of the aliphatically unsaturated compounds known in the art. Thus, the aliphatically unsaturated compound can be monomeric or polymeric material. It may contain only carbon and hydrogen or it may also contain another element or elements. Where the aliphatically unsaturated compound contains an element other than carbon and hydrogen, preferably the other element is oxygen, halogen, nitrogen, silicon or mixtures of these elements. Aliphatically unsaturated compounds can contain a single pair of carbon atoms linked by multiple bonds. Among the many unsaturated hydrocarbns applicable to the present invention can be mentioned for purposes of illustration; ethylene, propylene, butylene, octylene, styrene, butadiene, pentadiene, 2-pentene, 2-divinylbenzene, vinyl acetylene and the like. Preferably the unsaturated compound is one containing no more than about 18 carbon atoms in the chain.

Included in the oxygen containing unsaturated compounds which may be employed in the practice of the invention are methylvinyl ether, divinyl ether, pentavinyl ether; the monoallyl ether of ethylene glycol, allyl aldehyde, methylvinyl ketone, phenylvinyl ketone, acrylic acid, methacrylic acid, methacrylate, phenylmethacrylate, vinyl acetic acid, vinyl octoate, vinyl acetate, maleic acid, linoleic acid and the like. Other unsaturated compounds are acyclic and heterocyclic materials containing aliphatic unsaturation in the ring such as, cyclohexene, cycloheptene, cyclopentadiene, dihydrofuran, dihydropyrene and the like. The sulfur analogues of many of the unsaturated oxygen containing materials may also be employed in the practice of this invention. In addition to compounds containing carbon, hydrogen and oxygen, compounds containing other elements may also be used. Thus, halogenated derivatives of any of the materials described above can be employed including the acyl chlorides as well as compounds containing a halogen substituent on a carbon atom other than a carbonyl carbon atom. Thus, halogen containing materials include, for example, vinyl chloride, the vinyl chlorophenyl esters, the allyl esters, trichloroacetic acid and the like.

Other types of unsaturated materials which are useful in the practice of this invention include compounds containing nitrogen substituents such as acrylonitrile, allylcyanide, nitroethylene and the like. Unsaturated polymeric materials containing aliphatic unsaturation such as polyester resins prepared from polybasic saturated or unsaturated acids and polyhydric unsaturated alcohols may also be used in the practice of this invention.

Other unsaturated compounds which may be used in the practice of this invention are those compounds containing silicon such as the materials commonly referred to as organosilicon monomers or polymers. The scope of the organosilicon compounds which are applicable to the process is identical to the scope of the silicon hydrogen compound useful in the practice of this invention. For example, the unsaturated organosilicon compounds are identical to the silicon hydrogen, except that the silicon bonded hydrogen is replaced by silicon bonded organic radicals containing at least one pair of aliphatic carbon atoms linked with multiple bonds. Although it is preferred that the organosilicon compounds be free of silicon bonded hydrogen atoms, organosilicon compounds containing both silicon bonded hydrogens and silicon bonded unsaturated radicals may be used. The only requirement of these unsaturated silicon compounds is that there be at least one unsaturated organic radical attached to the silicon atom per molecule. Thus, the unsaturated organosilicon compounds include silanes, polysilanes, siloxanes, silazanes as well as monomeric or polymeric materials containing silicon atoms joined together by methylene or polymethylene groups or by phenylene groups.

Suitable organic compounds having an active hydrogen are alcohols, organic acids, polyethers and polyesters, diethylhydrogen phosphate, oximes and the like. Examples of alcohols are aliphatic alcohols having from 1 to 22 carbon atoms, methanol, butanol, octanol, dodecanol, cyclic aliphatic alcohols such as cyclohexanol, and aryl alcohols such as phenol.

Examples of suitable unsaturated silicon compounds which may be used are methylvinyldichlorosilane, vinyltrichlorosilane, allyltrichlorosilane, methylphenylvinylchlorosilane, phenylvinyldichlorosilane, diallychlorosilane, vinyl-beta-cyanoethyldichlorosilane, cyclic polysiloxanes such as cyclic trimer of methylvinylsiloxane, cyclic pentamer of methylvinylsiloxane, cyclic tetramer of methylvinylsiloxane, cyclic tetramer of vinylphenylsiloxane and the like.

The ratio of silicon hydrogen compound and unsaturated compound employed can vary within extremely wide limits. Generally, one silicon hydrogen bond is equivalent to one olefinic double bond or one-half acetylenic triple bond so that this equivalency establishes the general order of magnitude of the two reactants used. However, for many purposes it may be desirable to employ an excess of one of the reactants to facilitate the completion of the reaction or to insure that the reaction product contains either silicon hydrogen bonds in the unreacted state or contains one or more pairs of carbon atoms linked by multiple bonds. In general, however, the ratio of the reactants are selected so that there are present from about 0.5 to 20 silicon hydrogen linkages available for each unsaturated carbon-carbon double bond and from about 1.0 to 15 silicon hydrogen linkages for each carbon-carbon triple bond.

One of the advantages of the cobalt platinum catalyst of this invention is that it will produce the desired reaction between the silicon hydrogen compound and the unsaturated compound in very small quantities. Thus, the catalyst may be used in concentrations as low as 0.001 percent and up to about 5 percent by weight or higher based on the total weight of the unsaturated compound and the silcon hydrogen compound. Because of the economics, a particularly low level of catalyst, that is from about 0.5 to about 2 percent by weight is used. An additional advantage of employing a low concentration of catalyst is that it insures a low quantity of catalyst residue in the reaction product. Consequently, it has been found that satisfactory rates of reaction are obtained at reaction temperatures where about 0.02 to 2 percent by weight of catalyst are present.

Due to the fact that the catalyst is a solid material and is employed in minute quantities, it is desirable to use the catalyst as a dilute solution to facilitate uniform dispersion of the catalyst in the reaction medium. Suitable diluents are any materials which are solvents for the catalyst and which are inert to the reactants under the reaction conditions. The preferred diluents are hydrocarbon solvents such as aromatic hydrocarbons including benzene, toluene, xylene as well as aliphatic solvents such as aliphatic mineral spirits. In addition to these hydrocarbon solvents the diluent may be an alcohol or an ether such as isopropanol, octanol or tetrahydrofuran. Generally the amount of diluent will range from 0.1 to 5 percent by weight based on the weight of the catalyst.

To effect the addition reactions with the cobalt platinum catalyst of this invention, the reactants and the diluted catalyst are throughly mixed and the reaction mixture heated to the desired temperature which is generally of the order of from 50° to 150° C. and the reaction is allowed to go to completion. The time required for the addition reaction is a function of temperature. At a temperature of from about 50° to 80° C. which is the preferred range, the reaction times can vary from a few minutes up to 4 to 5 hours or more depending upon the reactants involved.

In some cases it is desirable to employ a solvent for one or both reactants. The amount of solvent employed is not critical and can vary over a wide range. Any solvent which is inert to the reactants and the reaction products can be employed. Obviously, the same material may in some cases serve both as the diluent and as the solvent.

The products prepared by the addition reactions of this invention have various utilities depending upon the particular product formed. Thus, the product formed from the monomeric silane containing a silicon bonded hydrogen atom and a silicon bonded hydrolyzable group and an olefinic material such as, for example, the product prepared by adding methyldichlorosilane to 1-octene may be hydrolyzed and condensed in conventional fashion to form various organopolysiloxanes which may be used as coating compositions and release agents. Similarly, the products may be used in conventional silicone polymer applications. Thus, these materials which are rubbery polymers can be used as gaskets and the like. Materials which are resinous in nature may be used in the formation of insulators for electrical conductors. In addition, the monomeric matierals produced by the addition reactions of the present invention are obviously valuable as intermediates in the preparation of more complicated materials.

Various embodiments of this invention are further illustrated in the following examples in which all parts are by weight unless otherwise specified.

EXAMPLE 1

To a reactor equipped with a condenser and a stirring apparatus and containing about 18 parts of tetrahydrofuran are added about 10 parts of platinum dichloride and about 12.8 parts of dicobalt octacarbonyl. The reactants are agitated and heated to about 52° C. for about 2 hours. The solvent is removed under vacuum at a temperature of about 65° C. The resulting product is washed with 250 parts of ligroin and dried under vacuum. A black solid residue is obtained which is soluble in isopropy alcohol. Analysis of the product is as follows:

|  | Actual | Theory |
|---|---|---|
| Platinum | 31.94% | 32.09% |
| Chlorine | 11.20% | 11.70% |
| Cobalt | 19.20% | 19.50% |

X-ray analysis of the product shows the absence of platinum dichloride bands.

EXAMPLE 2

The procedure of Example 1 is repeated except that diethylether is substituted for tetrahydrofuran. A black solid residue is obtained which is soluble in isopropyl alcohol.

EXAMPLE 3

The procedure of Example 1 is repeated except that isopropylether is substituted for tetrahydrofuran. A black solid residue is obtained which is soluble in isopropyl alcohol.

EXAMPLE 4

Approximately 0.014 parts of the platinum catalyst prepared in accordance with the procedure described in Example 1 are dissolved in about 20 parts of tetrahydrofuran and added to about 42 parts of 1-hexene and about 53 parts of dimethoxymethylsilane in about 100 parts of tetrahydrofuran. The reactants are heated to reflux temperature and refluxed for about 30 minutes. The solvent is removed under vacuum, yielding about 86 parts of a product identified as hexylethyldimethoxysilane.

In a comparison experiment 1.4 parts of dicobalt octacarbonyl are substituted for the platinum catalyst of Example 1. Approximately 8.9 percent of the addition product is obtained.

EXAMPLES 5 THRU 19

In accordance with the procedure discussed in Example 2, unsaturated organic compounds and compounds containing an active hydrogen are reacted with a compound containing an ≡Si—H group in the presence of the catalyst of Example 1. The results are illustrated in the Table.

| Ex. No. | Unsaturated Type | Compound Parts | Silicon-hydrogen Type | Compound Parts | Catalyst Parts | Reaction Solvent Type Parts | Conditions Time Hr. | Conditions Temp. | Product Compound | Addition |
|---|---|---|---|---|---|---|---|---|---|---|
| 3 | ethylene | 14 | trichlorosilane | 68 | .008 | THF | 2.0 | reflux | ethyltrichlorosilane | 60% |
| 4 | 1-butene | 28 | dimethylsilane | 30 | .006 | THF | 2.0 | reflux | butyldimethylsilane | 65% |
| 5 | 1-hexene | 42 | triethylsilane | 44 | .008 | THF | 2.0 | reflux | hexyltriethylsilane | 58% |
| 6 | 3-hexene | 42 | methyldichlorosilane | 58 | 0.01 | THF | 2.0 | reflux | hexamethyldichlorosilane | 64% |
| 7 | 1-octene | 56 | methyldiacetoxysilane | 81 | 0.13 | None | 2.5 | reflux | methyloctyldiacetoxysilane | 85% |
| 8 | 1-decene | 70 | propyldibutoxysilane | 113 | 0.18 | None | 2.7 | reflux | decylpropyldibutoxysilane | 87% |
| 9 | 1-dodecene | 84 | tetramethylhydrogendisiloxane | 59 | 0.14 | None | 2.7 | reflux | tetramethyldidocecyldisiloxane | 90% |
| 10 | 1-hexadecene | 112 | trichlorosilane | 68 | 0.17 | None | 3.0 | reflux | hexadecyltrichlorosilane | 90% |
| 11 | 1-eicosene | 14 | ethyldioctoxysilane | 88 | 0.22 | None | 4.0 | reflux | | |
| 12 | methanol | 13 | methyldichlorosilane | 115 | 0.12 | THF | 1.2 | reflux | methylmethoxydichlorosilane | 70% |
| 13 | ethanol | 27 | tetraphenylhydrogendisiloxane | 260 | 0.28 | THF | 1.4 | reflux | tetraphenyldiethoxydisiloxane | 90% |
| 14 | 1-butanol | 34 | tetramethylhydrogendisiloxane | 118 | 0.14 | THF | 1.7 | reflux | tetramethyldibutoxydisiloxane | 90% |
| 15 | acetic acid | 55 | triethylsilane | 115 | 0.16 | None | 2.0 | reflux | triethylacetoxysilane | 90% |
| 16 | styrene | 76 | ethyldimethoxysilane | 119 | 0.18 | None | 2.3 | reflux | ethyldimethoxyethylphenylsilane | 80% |
| 17 | methylvinyldichlorosilane | 26 | trichlorosilane | 68 | 0.08 | None | 1.2 | reflux | trichlorosilylethylmethyldichlorosilane | 75% |

When other silicon compounds containing a silicon to hydrogen linkage are reacted with other unsaturated organic compounds in the presence of the above identified platinum catalyst, addition products are obtained under substantially the same reaction conditions.

Although specific examples of the invention have been herein described, it is not intended to limit the invention solely thereto, but to include all the variations and modifications falling within the spirit and scope of the appended claims.

What is claimed is:

1. A method for preparing a cobalt-platinum catalyst which will catalyze the addition of SiH containing compounds to unsaturated organic compounds which consists essentially of reacting platinum dichloride with dicobalt octacarbonyl in a 1:1 mol ratio in the presence of an ether solvent having a boiling point up to about 102° C and at a temperature up to about 52° C.

2. The method of claim 1 wherein the reaction is conducted at a temperature of from 30° to 50° C.

3. The method of claim 1 wherein the ether is tetrahydrofuran.

4. The cobalt-platinum catalyst obtained from the method of claim 1.